United States Patent [19]

Coates et al.

[11] Patent Number: 5,047,404
[45] Date of Patent: Sep. 10, 1991

[54] CHEMICAL COMPOUNDS

[75] Inventors: William J. Coates; Sean T. Flynn; Derek A. Rawlings, all of Hertfordshire, England

[73] Assignee: Smith Kline & French Laboratories, Ltd., Welwyn Garden City, England

[21] Appl. No.: 365,469

[22] Filed: Jun. 13, 1989

[30] Foreign Application Priority Data

Jun. 16, 1988 [GB] United Kingdom ................ 8814350
Jun. 16, 1988 [GB] United Kingdom ................ 8814351
Jun. 16, 1988 [GB] United Kingdom ................ 8814353

[51] Int. Cl.$^5$ .................... A61K 31/44; C07D 475/02; C07D 487/04
[52] U.S. Cl. .................................. 514/243; 514/212; 514/234.2; 514/249; 514/254; 514/258; 544/279; 544/184; 544/257; 544/258; 544/112; 544/117; 544/118; 540/599; 540/600
[58] Field of Search .................... 514/212, 234.2, 243, 514/249, 254, 258; 544/279, 184, 257, 258, 112, 117, 118; 540/599, 600

[56] References Cited

U.S. PATENT DOCUMENTS 3,873,545  3/1975  Osselaere et al. ............ 260/256.5 R
3,895,012  7/1975  Liede et al. .......................... 544/257
4,361,700  11/1982  Purcell et al. ........................ 544/279

FOREIGN PATENT DOCUMENTS 2225166  11/1974  France .
1401463  7/1975  United Kingdom .
1543874  4/1979  United Kingdom .

OTHER PUBLICATIONS

Huang, J., "Synthesis of Fused ... Ring Systems", J. Org. Chem. 50, 2293 (1985).

Parish et al., "Synthesis and Diuretic Activity ... Related Compounds", J. Med. Chem., 25, 98 (1982).
Lunt, E., "Recent Advances in Anti-Allergic ... Pharmaceutical Research", Woolridge, K. R. H., Ed., Blackwell Scientific, vol. 4, 41 (1982).
Albert, A., "Pteridine Studies. Part 46. 2-Alkylpteridin ... Derivatives", J. Chem. Soc. (Perkin I), 1574 (1979).
Fossion et al., "Etude Pharmacologique ... pyrimidone-4", J. Pharm. Belg. 31, 51 (1976).
Yoneda et al., "A New Synthesis of Alloxazines ... Anilinouracils", J. Chem. Soc., (Perkin I), 1907 (1975).
Osselaere et al., "Derives de la (3H) Pyrido ... Diuretiques", Eur. J. Med. Chem.-Chimica Therapeutica, 9, 305 (1974).
Osselaere, J. P., "Nouveaux Derives des Aryl-2 ... Substituees en 4", J. Pharm. Belg., 29, 145 (1974).
Osselaere et al., "Derives des amino-4 ... spasmolytiques", Annales Pharm. Francaises, 32, 575 (1974).
Brugger et al., "Eine einfache 6-Aza-pteridin-Synthese", Liebigs Ann. Chem. 758, 173 (1972).
Clark et al., "Heterocyclic Studies. Part VIII. 2--Phenylpteridine and Some Related Compounds", J. Chem. Soc. (C) 1408 (1969).
Gelling et al., "Pyridopyrimidines. Part V. Syntheses and Properties ... (1H,3H)-diones", J. Chem. Soc. (C) · 931 (1969).
Ismail et al., "The Synthesis of Pyrido ... Nicotinic Acid", J. Chem. Soc., (C), 2613 (1967).

Primary Examiner—John M. Ford
Attorney, Agent, or Firm—Charles M. Kinzig; Stuart R. Suter; Edward T. Lentz

[57] ABSTRACT

This invention relates to fused pyrimidine derivatives which have bronchodilator and anti-allergic activities. A compound of the invention is 2-(2-propoxyphenyl)-pyrido[2,3-d]pyrimid-4(3H)-one.

19 Claims, No Drawings

CHEMICAL COMPOUNDS

The present invention relates to fused pyrimidine derivatives, intermediates in their preparation, pharmaceutical compositions containing them and a method of effecting bronchodilatation or of combatting allergic diseases by administering them. The compounds of this invention are inhibitors of a calmodulin insensitive cyclic GMP phosphodiesterase and are of use in combatting such conditions where such inhibition is thought to be beneficial. They are bronchodilators and are therefore of use in combatting chronic reversible obstructive lung diseases such as asthma and bronchitis. Some of the compounds of the present invention have anti-allergic activity and are therefore useful in combatting allergic diseases such as allergic asthma, allergic rhinitis, urticaria and irritable bowel syndrome. Furthermore the compounds of this invention are vasodilators and are therefore of value in combatting angina, hypertension and congestive heart failure.

Accordingly the present invention provides compounds of the formula (1):

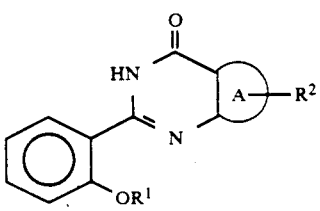

(1)

and pharmaceutically acceptable salts thereof, wherein

is a ring of sub-formula (a), (b), (c), (d), (e), (f) or (g):

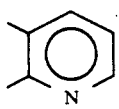 (a)

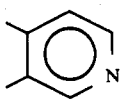 (b)

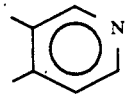 (c)

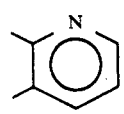 (d)

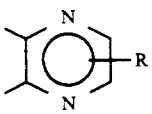 (e)

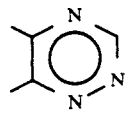 (f)

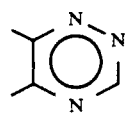 (g)

$R^1$ is $C_{1-6}$alkyl, $C_{2-6}$alkenyl, $C_{3-5}$cycloalkyl$C_{1-6}$alkyl, or $C_{1-6}$alkyl substituted by 1 to 6 fluoro groups;

$R^2$ is $C_{1-6}$alkylthio, $C_{1-6}$alkylsulphonyl, $C_{1-6}$alkoxy, hydroxy, hydrogen, hydrazino, $C_{1-6}$alkyl, phenyl, —NHCOR$^3$ wherein $R^3$ is hydrogen or $C_{1-6}$alkyl, or —NR$^4$R$^5$, wherein $R^4$ and $R^5$ together with the nitrogen atom to which they are attached form a pyrrolidino, piperidino, hexahydroazepino, morpholino or piperazino ring, or $R^4$ and $R^5$ are independently hydrogen, $C_{3-5}$cycloalkyl or $C_{1-6}$alkyl which is optionally substituted by —CF$_3$, phenyl, —S(O)$_n$C$_{1-6}$alkyl wherein n is 0, 1 or 2, —OR$^6$, —CO$_2$R$^7$ or —NR$^8$R$^9$ wherein $R^6$ to $R^9$ are independently hydrogen or $C_{1-6}$alkyl, provided that the carbon atom adjacent to the nitrogen atom is not substituted by said —S(O)$_n$C$_{1-6}$alkyl, —OR$^6$ or —NR$^8$R$^9$ groups; and R is hydrogen and can also be hydroxy when $R^2$ is hydroxy.

Suitably $R^1$ is $C_{2-5}$alkyl for example ethyl, n-propyl, isopropyl, butyl, isobutyl or pentyl.

Suitably $R^1$ is $C_{3-5}$alkenyl for example propenyl, butenyl or pentenyl.

Suitably $R^1$ is cyclopropylmethyl.

Examples of $C_{1-6}$alkyl substituted by 1 to 6 fluoro groups include —CF$_3$, —CH$_2$CF$_3$ or —CF$_2$CHFCF$_3$.

Preferably $R^1$ is n-propyl.

Suitably $R^2$ is $C_{1-6}$alkylthio, $C_{1-6}$alkylsulphonyl or $C_{1-6}$alkoxy for example methylthio, ethylthio, methylsulphonyl, ethylsulphonyl, methoxy, ethoxy or propoxy.

Suitably $R^2$ is hydroxy, hydrogen or hydrazino.

Suitably $R^2$ is phenyl or $C_{1-6}$alkyl for example methyl, ethyl or propyl.

Suitably $R^2$ is —NHCOR$^3$ for example formamido or acetamido.

Suitably $R^2$ is —NR$^4$R$^5$ for example amino, methylamino, ethylamino, propylamino, dimethylamino, diethylamino, dipropylamino, cyclopropylamino, morpholino, 2,2,2-trifluoroethylamino, phenethylamino, 3-methylthiopropylamino, 3-methylsulphinylpropylamino, 3-methylsulphonylpropylamino, 2-hydroxyethylamino, 3-hydroxypropylamino, 2-hydroxypropylamino, 3-methoxypropylamino, N-ethyl-N-(2-hydroxyethyl)amino, 2-aminoethylamino, 2-dimethylaminoethylamino, ethoxycarbonylmethylamino, carboxymethylamino, 2-ethoxycarbonylethylamino or 2-carboxyethylamino.

Suitably

is a group of sub-formula (a) thus forming a pyrido[2,3-d]pyrimidine ring system.

Suitably

is a group of sub-formula (b) thus forming a pyrido[3,4-d]pyrimidine ring system.

Suitably

is a group of sub-formula (c) thus forming a pyrido[4,3-d]pyrimidine ring system.

Suitably

is a group of sub-formula (d) thus forming a pyrido[3,2-d]pyrimidine ring system.

Suitably

is a group of sub-formula (e) thus forming a pteridine ring system.

Suitably

is a group of sub-formula (f) thus forming a pyrimido[5,4-e][1,2,4]triazine ring system.

Suitably

is a group of sub-formula (g) thus forming a pyrimido[4,5-e][1,2,4]triazine ring system.

Particular compounds of this invention are:
2-(2-propoxyphenyl)pyrido[2,3-d]pyrimid-4(3H)-one,
2-(2-propoxyphenyl)pyrido[3,4-d]pyrimid-4(3H)-one,
2-(2-propoxyphenyl)pyrido[4,3-d]pyrimid-4(3H)-one,
2-(2-propoxyphenyl)pyrido[3,2-d]pyrimid-4(3H)-one,
2-(2-propoxyphenyl)pteridin-4(3H)-one,
2-(2-propoxyphenyl)pteridin-4,6(3H,5H)-dione,
2-(2-propoxyphenyl)pteridin-4,6,7(3H,5H,8H)-trione,
5,6-dihydro-3-methylthio-5-oxo-7-(2-propoxyphenyl)-pyrimido[5,4-e][1,2,4]triazine,
3-amino-5,6-dihydro-5-oxo-7-(2-propoxyphenyl)-pyrimido[5,4-e][1,2,4]triazine,
3-methylamino-5,6-dihydro-5-oxo-7-(2-propoxyphenyl)pyrimido[5,4-e][1,2,4]triazine,
3-methoxy-5,6-dihydro-5-oxo-7-(2-propoxyphenyl)-pyrimido[5,4-e][1,2,4]triazine,
3-methylthio-8-oxo-6-(2-propoxyphenyl)-7,8-dihydropyrimido[4,5-e][1,2,4]triazine,
3-amino-8-oxo-6-(2-propoxyphenyl)-7,8-dihydropyrimido[4,5-e][1,2,4]triazine,
3-methylamino-8-oxo-6-(2-propoxyphenyl)-7,8-dihydropyrimido[4,5-e][1,2,4]triazine,
3-methoxy-8-oxo-6-(2-propoxyphenyl)-7,8-dihydropyrimido[4,5-e][1,2,4]triazine,
3,8-dioxo-6-(2-propoxyphenyl)-3,4,7,8-tetrahydropyrimido[4,5-e][1,2,4]triazine,
3-dimethylamino-8-oxo-6-(2-propoxyphenyl)-7,8-dihydropyrimido[4,5-e][1,2,4]triazine,
3-methylthio-8-oxo-6-(2-allyloxyphenyl)-7,8-dihydropyrimido[4,5-e][1,2,4]triazine,
3-methylthio-8-oxo-6-(2-isobutoxyphenyl)-7,8-dihydropyrimido[4,5-e][1,2,4]triazine,
3-methylthio-8-oxo-6-(2-cyclopropylmethoxyphenyl)-7,8-dihydropyrimido[4,5-e][1,2,4]triazine or
3-methylthio-8-oxo-6-(2-methoxyphenyl)-7,8-dihydropyrimido[4,5-e][1,2,4]triazine
or pharmaceutically acceptable salts thereof.

This invention covers all tautomeric and optical isomeric forms of compounds of formula (1).

Compounds of the formula (1) wherein $R^2$ is $-NR^4R^5$ or hydrazino may form pharmaceutically acceptable salts with acids such as hydrochloric, hydrobromic, sulphuric, methanesulphonic and phosphoric acids.

Compounds of the formula (1) may form pharmaceutically acceptable salts with metal ions, such as alkali metals for example sodium and potassium, or with an ammonium ion.

In order to use a compound of the formula (1) or a pharmaceutically acceptable salt thereof for the treatment of humans and other mammals it is normally formulated in accordance with standard pharmaceutical practice as a pharmaceutical composition Compounds of formula (1) and their pharmaceutically acceptable salts may be administered in standard manner for the treatment of the indicated diseases, for example orally, sublingually, parenterally, transdermally, rectally, via inhalation or via buccal administration.

Compounds of formula (1) and their pharmaceutically acceptable salts which are active when given orally or via buccal administration can be formulated appropriately in dosage forms such as liquids, syrups, tablets, capsules and lozenges. An oral liquid formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include starch, celluloses, lactose, sucrose and magnesium stearate Where the composition is in the form of a capsule, any routine encapsulation is suitable, for example using the aforementioned carriers in a hard gelatin capsule shell. Where the composition is in the form of a soft gelatin shell capsule, any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil or solubilising agent, for example polyethylene glycol, polyvinylpyrrolidone, lecithin, 2-pyrrolidone, cyclodextrin, arachis oil, or sesame oil.

A typical suppository formulation comprises a compound of formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane, or are in the form of a powder for insufflation.

Preferably the composition is in unit dosage form, for example a tablet, capsule or metered aerosol dose, so that the patient may administer to himself a single dose.

Each dosage unit for oral administration contains suitably from 0.001 mg/Kg to 30 mg/Kg, and preferably from 0.005 mg/Kg to 15 mg/Kg, and each dosage unit for parenteral administration contains suitably from 0.001 mg/Kg to 10 mg/Kg, of a compound of formula (1) or a pharmaceutically acceptable salt thereof calculated as the free base. The daily dosage regimen for oral administration is suitably about 0.001 mg/Kg to 120 mg/Kg, of a compound of formula (1) or a pharmaceutically acceptable salt thereof calculated as the free base. The daily dosage regimen for parenteral administration is suitably about 0.001 mg/Kg to 40 mg/Kg, for example about 0.005 mg/Kg to 10 mg/Kg, of a compound of the formula (1) or a pharmaceutically acceptable salt thereof calculated as the free base. The active ingredient may be administered as required for example from 1 to 8 times a day or by infusion. The compositions of the invention are bronchodilators and are useful in chronic reversible obstructive lung disease for example asthma and bronchitis. In addition some of the compositions of the present invention have anti-allergic activity and are useful in combatting allergic diseases such as allergic asthma, allergic rhinitis, urticaria and irritable bowel syndrome. The compositions of the present invention also have vasodilator activity and are of use in the treatment of angina, hypertension and congestive heart failure. Such conditions can be treated by administration orally, sublingually topically, rectally, parenterally or by inhalation. For administration by inhalation dosages are controlled by a valve, are administered as required and for an adult are conveniently in the range 0.1–5.0 mg of a compound of the formula (1) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a single pharmaceutical composition. Examples of compounds which may be included in pharmaceutical compositions with the compounds of the formula (1) are bronchodilators such as sympathomimetic amines for example isoprenaline, isoetharine, sulbutamol, phenylephrine and ephedrine or xanthine derivatives for example theophylline and aminophylline, anti-allergic agents for example disodium cromoglycate, histamine $H_1$-antagonists, vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (1) or pharmaceutically acceptable salts thereof can be prepared by a process which comprises:

a) cyclising a compound of the formula (2):

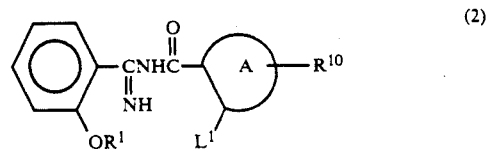

wherein $L^1$ is a displaceable group, $R^1$ and

are as hereinbefore defined, and $R^{10}$ is a group $R^2$ as hereinbefore defined or a precursor thereof; or b) cyclising a compound of the formula (3):

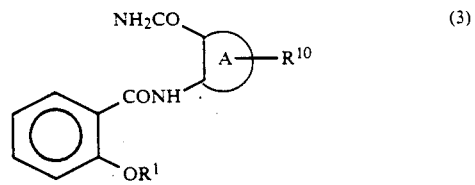

wherein $R^1$, $R^{10}$ and

are as hereinbefore defined;

c) for compounds wherein $R^2$ and R are both hydrogen, reacting a compound of the formula (4) with glyoxal or a chemical equivalent thereof:

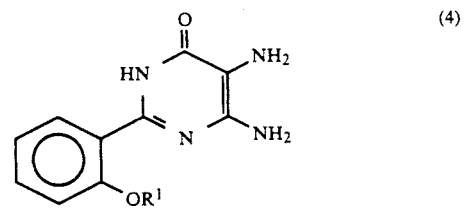

wherein $R^1$ is as hereinbefore defined;

d) for compounds wherein $R^2$ is 6-hydroxy and R is hydrogen, reacting a compound of the formula (4) as hereinbefore defined with chloral or a chemical equivalent thereof;

e) for compounds wherein $R^2$ and R are both hydroxy, reacting a compound of the formula (4) as hereinbefore defined with $(COL)_2$ wherein L is a leaving group;

and thereafter where necessary:
converting a group $R^{10}$ to a group $R^2$;
optionally forming a pharmaceutically acceptable salt.

Suitably the cyclisation of a compound of the formula (2) is performed in the presence of a base such as an alkali metal carbonate or triethylamine, in an aprotic solvent such as dimethylformamide, acetonitrile or N-methylpyrrolidone, at ambient or an elevated temperature, for example 50°–170° C., conveniently at the reflux temperature of the reaction mixture. Suitably $L^1$ is halo for example bromo or chloro.

Suitably a compound of the formula (3) is cyclised by heating at an elevated temperature, for example 50°–150° C., in the presence of an acid or a base in a suitable solvent such as aqueous $C_{1-4}$alcohols, water, toluene, a halohydrocarbon or acetonitrile. Conveniently a compound of the formula (3) is cyclised by heating in pyridine or aqueous base such as sodium hydroxide at the reflux temperature of the reaction mixture.

Suitably an acid addition salt (e.g. the sulphate or chloride) of a compound of the formula (4) is reacted with glyoxal hydrate or with chloral hydrate in a suitable solvent such as water or $C_{1-4}$alkanols or mixtures thereof at an elevated temperature e.g. 40°–150° C., conveniently at the reflux temperature of the reaction mixture.

Suitably a compound of the formula (4) is reacted with $(COL)_2$ in a solvent such as a $C_{1-4}$alkanol or $C_{1-4}$alkoxy$C_{1-4}$alkanol or mixtures thereof at an elevated temperature e.g. 40°–150° C., conveniently at the reflux temperature of the reaction mixture. Suitably L is $C_{1-6}$alkoxy such as methoxy or ethoxy or halo such as bromo or chloro.

Examples of $R^{10}$ being a precursor to a group $R^2$ is when $R^{10}$ is a halo or $C_{1-6}$alkylthio group. Such groups can be converted to a $-NR^4R^5$ group by reaction with an amine $HNR^4R^5$ in a suitable solvent such as a $C_{1-4}$alkanol or pyridine at an elevated temperature, for example 50°–120° C., conveniently in a pressure vessel.

A compound of the formula (1) wherein $R^2$ is $C_{1-6}$alkylthio can suitably be converted to the corresponding compound wherein $R^2$ is $C_{1-6}$alkylsulphonyl by reaction with an oxidising agent, for example with at least two equivalents of a peroxy acid such as m-chloroperoxybenzoic acid.

A compound of the formula (1) wherein $R^2$ is $C_{1-6}$alkylsulphonyl can suitably be converted to the corresponding compound wherein $R^2$ is $-NR^4R^5$ by reaction with an amine $HNR^4R^5$ in a suitable solvent such as a halohydrocarbon or toluene at ambient or elevated temperature for example 40°–100° C.

A compound of the formula (1) wherein $R^2$ is $C_{1-6}$alkylsulphonyl can suitably be converted to the corresponding compound wherein $R^2$ is $C_{1-6}$alkoxy by reaction with a $C_{1-6}$alkoxide, e.g. an alkali metal $C_{1-6}$alkoxide such as sodium methoxide or ethoxide, in a $C_{1-6}$alkanol at ambient or elevated temperature, for example 40°–100° C.

A compound of the formula (1) wherein $R^2$ is $C_{1-6}$alkylthio can suitably be converted to the corresponding compound wherein $R^2$ is hydrazino by reaction with hydrazine.

A compound of the formula (1) wherein $R^2$ is hydrazino can be converted to the corresponding compound wherein $R^2$ is hydrogen by treatment with silver oxide.

A compound of the formula (1) wherein $R^2$ is $C_{1-6}$alkoxy can suitably be prepared by reacting a compound of the formula (1) wherein $R^2$ is $C_{1-6}$alkylthio with an alkali metal $C_{1-6}$alkoxide such as sodium methoxide or ethoxide.

A compound of the formula (1) wherein $R^2$ is $C_{1-6}$alkoxy can be converted to the corresponding compound wherein $R^2$ is hydroxy by hydrolysis, for example by treatment with hydrochloric acid.

A compound of the formula (1) wherein $R^2$ is amino can suitably be converted to the corresponding compound where $R^2$ is $-NHCOR^3$ by reaction with a formylating or $C_{2-7}$alkanoylating agent Examples of such reagents include formic acid, $C_{1-6}$alkyl formate, formamide, acetic anhydride, propionic anhydride or acetylchloride.

A compound of the formula (1) wherein $R^4$ or $R^5$ is $C_{1-6}$alkyl substituted by $C_{1-6}$alkylthio can suitably be converted to the corresponding compound wherein $R^4$ or $R^5$ is $C_{1-6}$alkyl substituted by $C_{1-6}$alkylsulphinyl by reaction with one equivalent of an oxidising agent such as a peroxy acid, for example m-chloroperoxybenzoic acid. The $C_{1-6}$alkylsulphinyl compound can similarly be oxidised to a compound of the formula (1) wherein $R^4$ or $R^5$ is $C_{1-6}$alkyl substituted by $C_{1-6}$alkylsulphonyl.

A compound of the formula (1) wherein $R^4$ or $R^5$ is $C_{1-6}$alkyl substituted by $-CO_2R^7$ in which $R^7$ is $C_{1-6}$alkyl can suitably be hydrolysed by reaction with aqueous base, for example aqueous sodium hydroxide to form the corresponding compound wherein $R^7$ is hydrogen.

The compounds of the formula (2) can be prepared by reaction of a compound of the formula (5):

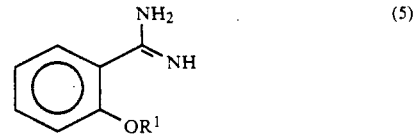

wherein $R^1$ is as hereinbefore defined,
with a compound of the formula (6):

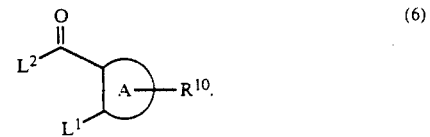

wherein $L^2$ is a leaving group and $L^1$, $R^{10}$ and

are as hereinbefore defined.

Suitably $L^2$ is $C_{1-6}$alkoxy or halo for example methoxy, ethoxy, chloro or bromo. Conveniently a solution of a compound of the formula (5) is initially formed by treatment of an acid addition salt of a compound of the formula (5) with a suitable base, for example triethylamine, a sodium alkoxide or sodium hydride, in an organic solvent such as a $C_{1-4}$alkanol, acetonitrile or dimethylformamide and the solution is then treated with a compound of the formula (6) at a moderate temperature for example 0°-60° C., conveniently ambient, to afford a compound of formula (2). Suitable acid addition salts are those formed with inorganic acids such as hydrochloric or sulphuric acid or with strong organic acids such as methanesulphonic or p-toluenesulphonic acid. Suitably a compound of the formula (2) is isolated and is then cyclised as hereinbefore described. Alternatively, a compound of the formula (2) is not isolated but is cyclised in situ by stirring at ambient or an elevated temperature, for example 40°-170° C.

A compound of the formula (3) can be prepared by reaction of a compound of the formula (7):

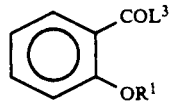   (7)

wherein $R^1$ is as hereinbefore defined and $L^3$ is halo, with a compound of the formula (8):

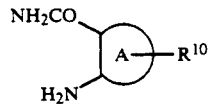   (8)

wherein $R^{10}$ and

are as hereinbefore defined.

Suitably $L^3$ is chloro or bromo. Suitably a compound of the formula (7) is reacted with a compound of the formula (8) at ambient or elevated temperature e.g. 50°-100° C. in a suitable solvent such as toluene, acetonitrile or a halohydrocarbon e.g. chloroform or dichloromethane, optionally in the presence of a base such as pyridine or triethylamine, to form a compound of the formula (3) which may be cyclised in situ or may be isolated and thereafter cyclised as hereinbefore described.

The compounds of the formulae (4) and (5) and acid addition salts thereof are known or preparable in conventional manner from U.S. Pat. No. 3819631.

The compound of the formula (6), (7) and (8) are known or can be prepared by methods known in the art, for example in J. Org. Chem., 19, 1633, (1954); J. Org. Chem., 17, 542, (1952); J. Am. Chem. Soc., 78, 973, (1956); Chem. Ber., 96, 266, (1963); J. Chem. Soc. Perkin Trans. 1 (6), 1574 (1979); J. Org. Chem., 50, 2293-2298 (1985), J. Org. Chem., 37, 3958 (1972), J. Org. Chem., 34, 2102 (1969), Aust. J. Chem. 1974, 27, 1781-90, Aust. J. Chem. 1973, 26, 1689, and J. Heterocycl. Chem. 1968, 5, 581.

Pharmaceutically acceptable acid addition salts of the compounds of the formula (1) wherein $R^2$ is $-NR^4R^5$ or hydrazino may be prepared from the corresponding base of the compounds of the formula (1) in conventional manner. For example the base may be reacted with an acid in a $C_{1-4}$ alkanol, or an ion-exchange resin may be used. The salts of the compounds of the formula (1) may be interconverted using ion-exchange resins. Non-pharmaceutically acceptable salts are therefore of use as they can be converted to pharmaceutically acceptable salts.

Pharmaceutically acceptable base addition salts of the compounds of the formula (1) may be prepared by standard methods, for example by reacting a solution of the compound of the formula (1) with a solution of the base.

The following biological test methods, data and Examples serve to illustrate this invention.

Bronchodilatation—In vivo

Male guinea-pigs of the Dunkin Hartley strain (500-600 g) were anaesthetised with Sagatal (pentobarbital sodium) (60 mg/kg). Airway resistance was measured using a modification of the classical Konzett-Rossler technique (J. Pharm. Methods, 13, 309-315, 1985). U46619 (9,11-methaneoepoxy-PGH$_2$) was infused i.v. at a rate of 2.5 nmol/min, this produced a steady state of bronchoconstriction (approximately 120% increase from basal airway resistance). The compound under test was administered by i.v. bolus injection, and the subsequent peak inhibition of bronchoconstriction recorded.

The dose of compound required to reduce the $U^{46619}$-induced bronchoconstriction by 50% is given as the BD$_{50}$. The compounds of Examples 1, 2 and 9 had BD$_{50}$ values in the range $2.8 \geq 4.9$ μmol/kg. These results demonstrate in vivo antibronchoconstrictor activity.

Vasodilatation—In vivo

Male Wistar rats (300 g) were anaesthetised with a sodium 5-ethyl-5-(I-methylpropyl)-2-thiobarbiturate/sodium pentobarbitone mixture i.p. (62.5 and 22.5 mg/kg respectively). The trachea was cannulated and the rats breathed spontaneously air enriched with O$_2$ (5 ml/min). Blood pressure was recorded from a carotid artery and a jugular vein was cannulated for the administration of compounds. The temperature of the animal was maintained at 37° C. by the use of an electric blanket. The abdominal aorta was separated from the inferior vena cava, distal to the renal arteries and was cannulated centrally to supply the perfusion pump with blood and distally for the perfusion of the hind quarters at constant pressure. The perfusion circuit was primed with 5% bovine serum albumin dissolved in 0.9% sodium chloride solution, pH adjusted to 7.4. Initially the pump rate was set between 10 and 15 ml/min to match the hind quarter perfusion pressure to that of the systemic circulation. Once set, the pressure remained unaltered for the rest of the experiment. A change in the speed of the pump (equivalent to hindquarter blood flow) was used to assess the changes in hindquarter vascular resistance. All compounds were administered as a bolus i.v. The compound of Example 12 caused a 38% increase in hindquarter blood flow at a dose of 10 μmol/kg.

Anti-allergic activity

Male Duncan Hartley guinea-pigs (250-300 g) were sensitised to ovalbumen by i.p. injection of 2 ml of 50 mg.ml$^{-1}$ i.p. and 0.2 ml s.c. Three weeks later they were anaesthetised with 60 mg.kg$^{-1}$ sodium pentabarbitone. The trachea was cannulated and the animal respired at a rate of 40 breaths per minute and at an initial tracheal inflation pressure of 16 mmHg. Tracheal inflation pressure was measured by a transducer connected to a side arm of the respiration circuit. The carotid artery was cannulated for the measurement of blood pressure and the signal was used to trigger an instantaneous rate meter. A jugular vein was cannulated for the administration of drug and allergen. After surgery the animals were allowed to stabilise and the drug was administered i.v. as a bolus. Following this, ovalbumen 1 mg.kg$^{-1}$ was injected i.v. as the antigen challenge either 2, 15 or 30 minutes following drug treatment and the peak bronchoconstrictor response recorded. For the control group ovalbumen only was given. One ovalbumen challenge per guinea-pig was used and n=6 for each time point. The percentage increase in tracheal inflation pressure was calculated. The following results indicating an anti-allergic activity were obtained.

| Compound of Example | Dose μmol/kg | % Inhibition of Control Bronchoconstrictor Response 30 min after drug administration |
| --- | --- | --- |
| 1 | 28 | 9 |

Phosphodiesterase activity

The activity of the compounds of the present invention as inhibitors of a calmodulin insensitive cyclic GMP phosphodiesterase was measured using the procedure described in European Patent Application No. 293063. The compounds of Examples 1-4, 6, 7, 10, 11 and 13-20 had IC$_{50}$ values (the concentration of inhibitor required for 50% inhibition of enzyme activity) in the range 0.55 to 11.38 μM. The compounds of the present invention have the advantage that they are selective in not inhibiting cyclic AMP phosphodiesterase (type III).

EXAMPLE 1

2-(2-Propoxyphenyl)pyrido[2,3-d]pyrimid-4(3H)-one a) A solution of 2-propoxybenzoyl chloride (0.99 g) in acetonitrile (7.5 ml) was added dropwise over 5 minutes to a cooled (0° C.), stirred mixture of 2-aminonicotinamide (0.69 g) and triethylamine (0.51 g) in acetonitrile (7.5 ml). The reaction mixture was stirred at ambient temperature for 1.5 hours, allowed to stand overnight and then evaporated under reduced pressure to dryness. The residue was washed with water to afford a solid (1.63 g) which was twice recrystallised from methanol to afford 2-(2-propoxybenzamido)nicotinamide, 0.92 g, m.p. 181°-184° C.

b) A stirred mixture of 2-(2-propoxybenzamido)-nicotinamide (0.77 g) and pyridine (0.8 ml) in 2 Normal sodium hydroxide (20 ml) was heated under reflux for 30 minutes. The cooled reaction mixture was neutralised with 2 Normal hydrochloric acid to afford a precipitate which together with another precipitate similarly prepared from 2-(2-propoxybenzamido)nicotinamide (0.1 g) was recrystallised from ethanol-ether to afford white needles (0.65 g) which were washed with water to afford the title compound, 0.55 g. m.p. 110°-111° C.

EXAMPLE 2

2-(2-Propoxyphenyl)pyrido[3,4-d]pyrimid-4(3H)-one a) In a similar manner to Example 1 a) reaction of 2-propoxybenzoyl chloride (0.99 g), 3-aminoisonicotinamide (0.69 g) and triethylamine (0.51 g) in acetonitrile (15 ml) afforded a crude product (1.45 g) which was recrystallised from methanol to afford 3-(2-propoxybenzamido)isonicotinamide, 0.73 g, m.p. 214°-7° C.

b) In a similar manner to Example 1 b) cyclisation of 3-(2-propoxybenzamido)isonicotinamide (0.72 g) afforded a crude product which was recrystallised from ethanol-water to afford the title compound, 0.44 g, m.p. 181°-183° C.

EXAMPLE 3

2-(2-Propoxyphenyl)pyrido[4,3-d]pyramid-4(3H)-one a) In a similar manner to Example 1 a) reaction of 2-propoxybenzoyl chloride (0.79 g), 4-aminonicotinamide (0.55 g) and triethylamine (0.40 g) in acetonitrile (12 ml) afforded a crude product which was recrystallised from ethanol-ether to afford 4-(2-propoxybenzamido)nicotinamide, 0.53 g, m.p. 164°-166° C.

b) In a similar manner to Example 1 b) cyclisation of 4-(2-propoxybenzamido)nicotinamide (0.52 g) afforded a crude product which was recrystallised from ethanol-water to afford the title compound, 0.45 g, m.p. 135°-136° C.

EXAMPLE 4

2-(2-Propoxyphenyl)pyrido[3,2-d]pyrimid-4(3H)-one a) In a similar manner to Example 1 a) reaction of 2-propoxybenzoyl chloride (0.99 g), 3-aminopicolinamide (0.69 g) and triethylamine (0.51 g) in acetonitrile (15 ml) afforded a crude product which was recrystallised from methanol to afford 3-(2-propoxybenzamido)-picolinamide, 0.91 g, m.p. 116°-118° C.

b) In a similar manner to Example 1 b) cyclisation of 3-(2-propoxybenzamido)picolinamide (0.90 g) afforded a crude product which was recrystallised from ethanol-water to afford the title compound, 0.28 g, m.p. 126°-127° C. The mother liquor was evaporated under reduced pressure to dryness and the residue recrystallised from ethanol-water to afford a further sample of the title compound, 0.46 g, m.p. 125°-126.5° C.

EXAMPLE 5

2-(2-Propoxyphenyl)pteridin-4(3H)-one

A stirred mixture of 4,5-diamino-2-(2-propoxyphenyl)pyrimidin-6-one sulphate (1.25 g), glyoxal hydrate (0.4 g), water (62.5 ml) and n-butanol (1 ml) was heated under reflux for one hour to afford a crude product (0.97 g) which was collected and washed with water. The crude product together with another sample (0.12 g) similarly prepared was eluted from a silica column with chloroform. The combined fractions containing product were evaporated under reduced pressure to afford a solid (0.96 g) which was recrystallised from ethanol-water to afford the title compound, 0.8 g, m.p. 177.5°-178.5° C.

EXAMPLE 6

2-(2-Propoxyphenyl)pteridin-4,6(3H,5H)-dione

A solution of chloral hydrate (1.74 g) in 50% aqueous methanol (10 ml) was added over 10 minutes to a stirred solution of 4,5-diamino-2-(2-propoxyphenyl)pyrimidin-6-one sulphate (1.89 g) in 50% aqueous methanol (60 ml) at 80° C. and the reaction mixture was stirred at 80° C. for 1.5 hours. The cooled reaction mixture was filtered to remove an orange brown solid which was discarded. On standing overnight the filtrate afforded a crude solid product (0.96 g) which was collected and washed with dilute aqueous potassium bicarbonate and water. The crude product together with another sample (0.20 g) similarly prepared was eluted from a silica column with chloroform. The combined fractions containing product were evaporated under reduced pressure to afford a solid (0.54 g) which was recrystallised from acetonitrile to afford the title compound, 0.39 g, m.p. 232°–233.5° C.

EXAMPLE 7

2-(2-Propoxyphenyl)pteridin-4,6,7(3H,5H,8H)-trione

A stirred mixture of 4,5-diamino-2-(2-propoxyphenyl)pyrimidin-6-one sulphate (1.0 g), triethylamine (0.42 ml) and diethyl oxalate (1.2 ml) in methoxyethanol (10 ml) was heated under reflux for 7 hours. The reaction mixture was stirred overnight at ambient temperature and a precipitate was collected and washed with water and ethanol to afford a crude product (0.70 g, m.p. 312°–315° C.). The crude product together with another sample (0.34 g) similarly prepared was twice recrystallised from dimethylformamide to afford the title compound, 0.40 g, m.p. 320°–321° C.

EXAMPLE 8

5,6-Dihydro-3-methylthio-5-oxo-7-(2-propoxyphenyl)-pyrimido[5,4-e][1,2,4]triazine a) A filtered solution of 2-propoxybenzamidine in ethanol (prepared from sodium, 0.28 g, in ethanol, 50 ml, and 2-propoxybenzamidine hydrochloride, 2.63 g) was added to a stirred, cooled solution of ethyl 3-chloro-6-methylthio-1,2,4-triazine-5-carboxylate (2.6 g) in ethanol (50 ml). After one hour the temperature was allowed to rise to ambient, stirred for a further one hour, then filtered to give 6-chloro-3-methylthio-5-(2-propoxybenzamidinocarbonyl)-1,2,4-triazine, 3.45 g, m.p. 229°–230° C.

b) A stirred mixture of the product from (a) above (3.45 g), potassium carbonate (1.3 g) and dimethylformamide (200 ml) was heated at 150° C. for 6.5 hours. Potassium carbonate (1.3 g) was added and the mixture was heated for a further 2 hours. Water (150 ml) was added to the residue left after evaporation, and the mixture was acidified with acetic acid to give 5,6-dihydro-3-methylthio-5-oxo-7-(2-propoxyphenyl)-pyrimido[5,4-e][1,2,4]triazine, 2.88 g, m.p. 195°–197° C. Recrystallisation from ethanol gave the pure product m.p. 224°–225° C.

EXAMPLE 9

3-Amino-5,6-dihydro-5-oxo-7-(2-propoxyphenyl)-pyrimido[5,4-e][1,2,4]triazine 5,6-Dihydro-3-methylthio-5-oxo-7-(2-propoxyphenyl)pyrimido[5,4-e][1,2,4]triazine (0.7 g) was heated for 30 hours with ethanolic ammonia (50 ml) at 100° C. in a pressure vessel. The cooled mixture was filtered to give the crude product (0.21 g) which was recrystallised from ethanol to give the pure title compound, m.p. 322°–325° C.

EXAMPLE 10

3-Methylamino-5,6-dihydro-5-oxo-7-(2-propoxyphenyl)pyrimido[5,4-e][1,2,4]triazine 5,6-Dihydro-3-methylthio-5-oxo-7-(2-propoxyphenyl)pyrimido[5,4-e][1,2,4]triazine (340 mg) was treated with a solution of methylamine in industrial methylated spirit (33%, 15 ml) at 70° C. in a pressure vessel (172 kPa) for 10 hours. The cooled reaction mixture was evaporated under reduced pressure to afford a yellow solid (290 mg) which was recrystallised from ethanol and then acetonitrile to afford the title compound, 120 mg, m.p. decomposes over 260° C.

EXAMPLE 11

3-Methoxy-5,6-dihydro-5-oxo-7-(2-propoxyphenyl)-pyrimido[5,4-e][1,2,4]triazine

A stirred mixture of 5,6-dihydro-3-methylthio-5-oxo-7-(2-propoxyphenyl)pyrimido[5,4-e][1,2,4]triazine (0.80 g) and sodium methoxide (prepared from sodium, 0.28 g and methanol) in methanol (50 ml) was heated under reflux for 1.5 hours. The cooled reaction mixture was neutralised by the addition of glacial acetic acid (0.7 ml) to afford a yellow precipitate (0.63 g) which was recrystallised from methanol to afford the title compound, 0.47 g, m.p. 221°–°222° C.

EXAMPLE 12

3-Methylthio-8-oxo 6-(2-propoxyphenyl)-7,8-dihydropyrimido[4,5-e][1,2,4]triazine A solution of 2-propoxybenzamidine (from 2.9 g of the hydrochloride) in 2-propanol (50 ml) was added at 2° C. to a solution of 3-methylthio-5-chloro-6-carboethoxy-1,2,4-triazine (2.08 g) in 2-propanol (100 ml). The mixture was stirred at 2° C. for 2 hours, allowed to stand at room temperature overnight, and then heated under reflux for 3 hours. The residue left after evaporation was dissolved in chloroform and the solution was washed with dilute hydrochloric acid. Evaporation of the chloroform and treatment of the residue with ethanol gave a solid (0.2 g) which was recrystallised from ethanol to give 3-methylthio-8-oxo-6-(2-propoxyphenyl)-7,8-dihydropyrimido[4,5-e][1,2,4]triazine, 0.12 g, m.p. 247°–249° C.

EXAMPLE 13

3-Amino-8-oxo-6-(2-propoxyphenyl)-7,8-dihydropyrimido[4,5-e][1,2,4]triazine

In a similar manner to that described in Example 10, 3-methylthio-8-oxo-6-(2-propoxyphenyl)-7,8-dihydropyrimido[4,5-e][1,2,4]triazine (1.42 g) was reacted with ethanolic ammonia (70 ml) for 20 hours to give the crude title compound, (0.80 g) which together with another sample (0.17 g), similarly prepared, was recrystallised from ethanol to afford the title compound, 0.54 g, m.p. 255°–256° C.

EXAMPLE 14

3-Methylamino-8-oxo-6-(2-propoxyphenyl)-7,8-dihydropyrimido[4,5-e][1,2,4]triazine 3-Methylthio-8-oxo-6-(2-propoxyphenyl)-7,8-dihydropyrimido[4,5-e][1,2,4]triazine (2.0 g) was treated with a solution of methylamine in industrial methylated spirit (33%, 30 ml) at 75° C. in a pressure vessel for 20 hours. The cooled reaction mixture was evaporated under reduced pressure to afford an oily solid which was dissolved in chloroform. The organic solution was washed with water, dried and evaporated under reduced pressure to afford a yellow oily solid which was eluted from a silica column with chloroform/methanol (5%). The fractions containing product were combined and evaporated under reduced pressure to afford a yel-

EXAMPLE 15

3-Methoxy-8-oxo-6-(2-propoxyphenyl)-7,8-dihydropyrimido[4,5-e][1,2,4]triazine

In a similar manner to Example 11, 3-methylthio-8-oxo-6-(2-propoxyphenyl)-7,8-dihydropyrimido[4,5-e][1,2,4]triazine (0.5 g) was treated for 3 hours with sodium methoxide (prepared from sodium, 0.17 g, and methanol) to afford the title compound, 0.34 g, m.p. 234°–235° C. (recrystallised from methanol).

EXAMPLE 16

3,8-Dioxo-6-(2-propoxyphenyl)-3,4,7,8-tetrahydropyrimido[4,5-e][1,2,4]triazine

A stirred mixture of 3-methylthio-8-oxo-6-(2-propoxyphenyl)-7,8-dihydropyrimido[4,5-e][1,2,4]triazine (0.5 g) and sodium methoxide (prepared from sodium, 0.17 g, and methanol) in methanol (50 ml) was heated under reflux for 3 hours. The cooled reaction mixture was evaporated under reduced pressure to afford a yellow solid which was dissolved in water and acidified with 2 Normal hydrochloric acid to yield a yellow solid (420 mg) which was recrystallised from dimethylformamide to afford the title compound, 0.16 g, m.p. 298°–299° C.

EXAMPLE 17

3-Dimethylamino-8-oxo-6-(2-propoxyphenyl)-7,8-dihydropyrimido[4,5-e][1,2,4]triazine 3-Methylthio-8-oxo-6-(2-propoxyphenyl)-7,8-dihydropyrimido[4,5-e][1,2,4]triazine (0.6 g) was treated with a solution of dimethylamine in industrial methylated spirit (33%, 20 ml) at 100° C. in a pressure vessel for 24 hours. The cooled reaction mixture was evaporated under reduced pressure to afford a yellow solid residue which was dissolved in dilute aqueous sodium hydroxide and filtered. The filtrate was acidified with a few drops of concentrated hydrochloric acid to afford a yellow precipitate which was collected, washed with water and recrystallised from methanol to afford the title compound, 0.44 g, m.p. 257.5°–259° C.

EXAMPLE 18

3-Methylthio-8-oxo-6-(2-allyloxyphenyl)-7,8-dihydropyrimido[4,5-e][1,2,4]triazine A cooled (5° C.) solution of 3-methylthio-5-chloro-6-carboethoxy-1,2,4-triazine (prepared by heating 3-methylthio-5-oxo-6-carboethoxy-4,5-dihydro-1,2,4-triazine, 1.5 g, with thionyl chloride, 30 ml, under reflux for two hours and thereafter removing thionyl chloride) in acetonitrile (30 ml) was added to a cooled stirred mixture of 2-allyloxybenzamidine hydrochloride (2.23 g) and triethylamine (1.06 g) in acetonitrile (50 ml). The mixture was stirred with cooling (0°–5° C.) for 15 minutes, then more triethylamine (0.71 g) was added and the reaction mixture was stirred at ambient temperature for two hours and left standing overnight. A yellow precipitate was collected, washed with water and recrystallised from acetonitrile and then from acetonitrile/ethanol (50%) to afford the title compound, 0.35 g, m.p. 238°–239° C.

EXAMPLE 19

3-Methylthio-8-oxo-6-(2-isobutoxyphenyl)-7,8-dihydropyrimido[4,5-e][1,2,4]triazine In a similar manner to Example 18 reaction of 3-methylthio-5-chloro-6-carboethoxy-1,2,4-triazine (prepared from 3-methylthio-5-oxo-6-carboethoxy-4,5-dihydro-1,2,4-triazine, 1.5 g) with 2-isobutoxybenzamidine hydrochloride (2.37 g) and triethylamine (1.75 g) afforded the crude title compound (1.71 g). This was recrystallised from acetonitrile, then dissolved in chloroform, the organic solution was washed with 2 Normal hydrochloric acid (x 2), chloroform removed under reduced pressure and the residue recrystallised twice from ethanol to afford the title compound, 0.32 g, m.p. 237°–238° C.

EXAMPLE 20

3-Methylthio-8-oxo-6-(2-cyclopropylmethoxyphenyl)-7,8-dihydropyrimido[4,5-e][1,2,4]triazine In a similar manner to Example 18 reaction of 3-methylthio-5-chloro-6-carboethoxy-1,2,4-triazine (prepared from 3-methylthio-5-oxo-6-carboethoxy-4,5-dihydro-1,2,4-triazine, 1.5 g) with 2-cyclopropoxybenzamidine hydrochloride (2.35 g) and triethylamine (1.75 g) afforded a yellow solid (1.31g) which was recrystallised from acetonitrile and then from acetonitrile/ethanol (50%) to afford the title compound, 0.70 g, m.p. 235–236° C.

EXAMPLE 21

3-Methylthio-8-oxo-6-(2-methoxyphenyl)-7,8-dihydropyrimido[4,5-e][1,2,4]triazine A cooled (0° C.) solution of 2-methoxybenzamidine (from 1.97 g of the hydrochloride) in acetonitrile (17 ml) was added to a cooled solution of 3-methylthio-5-chloro-6-carboethoxy-1,2,4-triazine (prepared from 3-methylthio-5-oxo-6-carboethoxy-4,5-dihydro-1,2,4-triazine, 1.08 g, and thionyl chloride, 20 ml) in acetonitrile (17 ml). Triethylamine (0.51 g) was added and the reaction mixture was stirred with cooling (0° C.) for one hour and then at ambient temperature for 17 hours to afford a yellow solid which was washed with acetonitrile and ether to afford the crude title compound (1.39 g). A sample (0.35 g) of this was washed twice with boiling methanol to afford the title compound, 0.25 g, m.p. 267.5°–268.5° C. The remaining material (1.04 g) was similarly treated with boiling methanol to afford the title compound, 0.91 g, m.p. 266°–268° C.

EXAMPLE 22

Pharmaceutical compositions for oral administration are prepared by combining the following:

| | % w/w | | |
|---|---|---|---|
| 2-(2-Propoxyphenyl)pyrido-[2,3-d]pyrimid-4(3H)-one | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

EXAMPLE 23

A pharmaceutical composition for parenteral administration is prepared by dissolving the title compound of Example 9 (0.02 g) in polyethylene glycol 300 (25 ml) with heating. This solution is then diluted with water for injections Ph. Eur. (to 100 ml). The solution is then sterilised by filtration through a 0.22 micron membrane filter and sealed in sterile containers.

What is claimed is:

1. A compound of the formula (1):

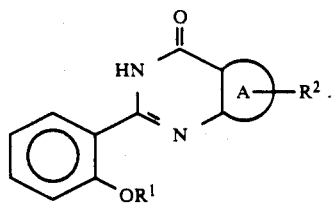

(1)

or a pharmaceutically acceptable salt thereof, wherein

is a ring of sub-formula (a), (b), (c), (d), (e), (f) or (g):

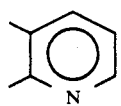 (a)

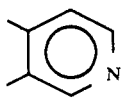 (b)

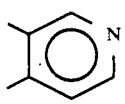 (c)

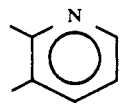 (d)

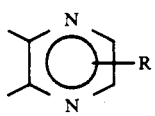 (e)

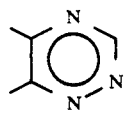 (f)

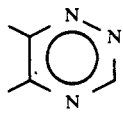 (g)

$R^1$ is $C_{1-6}$alkyl, $C_{2-6}$alkenyl, $C_{3-5}$cycloalkyl$C_{1-6}$alkyl, or $C_{1-6}$alkyl substituted by 1 to 6 fluoro groups;

$R^2$ is $C_{1-6}$alkylthio, $C_{1-6}$alkylsulphonyl, $C_{1-6}$alkoxy, hydroxy, hydrogen, hydrazino, $C_{1-6}$alkyl, phenyl, —NHCOR$^3$ wherein $R^3$ is hydrogen or $C_{1-6}$alkyl, or —NR$^4$R$^5$, wherein $R^4$ and $R^5$ together with the nitrogen atom to which they are attached form a pyrrolidino, piperidino, hexahydroazepino, morpholino or piperazino ring, or $R^4$ and $R^5$ are independently hydrogen, $C_{3-5}$cycloalkyl or $C_{1-6}$alkyl which is optionally substituted by —CF$_3$, phenyl, —S(O)$_n$C$_{1-6}$alkyl wherein n is 0, 1 or 2, —OR$^6$, —CO$_2$R$^7$ or —NR$^8$R$^9$ wherein $R^6$ to $R^9$ are independently hydrogen or $C_{1-6}$alkyl, provided that the carbon atom adjacent to the nitrogen atom is not substituted by said —S(O)$_n$C$_{1-6}$alkyl, —OR$^6$ or —NR$^8$R$^9$ groups; and R is hydrogen and can also be hydroxy when $R^2$ is hydroxy.

2. A compound according to claim 1 wherein $R^1$ is $C_{2-5}$alkyl.

3. A compound according to claim 1 wherein $R^1$ is n-propyl.

4. A compound according to claim 1 wherein $R^2$ is $C_{1-6}$alkylthio, $C_{1-6}$alkylsulphonyl or $C_{1-6}$alkoxy.

5. A compound according to claim 1 wherein $R^2$ is hydrogen, hydroxy or hydrazino.

6. A compound according to claim 1 wherein $R^2$ is phenyl or $C_{1-6}$alkyl.

7. A compound according to claim 1 wherein $R^2$ is —NHCOR$^3$ or —NR$^4$R$^5$.

8. A compound according to claim 1 wherein

is a group of sub-formula (a).

9. A compound according to claim 1 wherein

is a group of sub-formula (b).

10. A compound according to claim 1 wherein

is a group of sub-formula (c).

11. A compound according to claim 1 wherein

is a group of sub-formula (d).

12. A compound according to claim 1 wherein

is a group of sub-formula (e).

13. A compound according to claim 1 where

is a group of sub-formula (f).

14. A compound according to claim 1 wherein

is a group of sub-formula (g).

15. A compound according to claim 1 which is selected from the group consisting of:
2-(2-propoxyphenyl)pyrido[2,3-d]pyrimid-4(3H)-one,
2-(2-propoxyphenyl)pyrido[3,4-d]pyrimid-4(3H)-one,
2-(2-propoxyphenyl)pyrido[4,3-d]pyrimid-4(3H)-one,
2-(2-propoxyphenyl)pyrido[3,2-d]pyrimid-4(3H)-one,
2-(2-propoxyphenyl)pteridin-4(3H)-one,
2-(2-propoxyphenyl)pteridin-4,6(3H,5H)-dione,
2-(2-propoxyphenyl)pteridin-4,6,7(3H,5H,8H)-trione,
5,6-dihydro-3-methylthio-5-oxo-7-(2-propoxyphenyl)-pyrimido[5,4-e][1,2,4]triazine,
3-amino-5,6-dihydro-5-oxo-7-(2-propoxyphenyl)-pyrimido[5,4-e][,1,2,4]triazine,
3-methylamino-5,6-dihydro-5-oxo-7-(2-propoxyphenyl)pyrimido[5,4-e][1,2,4]triazine,
3-methoxy-5,6-dihydro-5-oxo-7-(2-propoxyphenyl)-pyrimido[5,4-e][1,2,4]triazine,
3-methylthio-8-oxo-6-(2-propoxyphenyl)-7,8-dihydropyrimido[4,5-e][1,2,4]triazine,
3-amino-8-oxo-6-(2-propoxyphenyl)-7,8-dihydropyrimido[4,5-e][1,2,4]triazine,
3-methylamino-8-oxo-6-(2-propoxyphenyl)-7,8-dihydropyrimido[4,5-e][1,2,4]triazine,
3-methoxy-8-oxo-6-(2-propoxyphenyl)-7,8-dihydropyrimido[4,5-e][1,2,4]triazine,
3,8-dioxo-6-(2-propoxyphenyl)-3,4,7,8-tetrahydropyrimido[4,5-e][1,2,4]triazine,
3-dimethylamino-8-oxo-6-(2-propoxyphenyl)-7,8-dihydropyrimido[4,5-e][1,2,4]triazine,
3-methylthio-8-oxo-6-(2-allyloxyphenyl)-7,8-dihydropyrimido[4,5-e][1,2,4]triazine,
3-methylthio-8-oxo-6-(2-isobutoxyphenyl)-7,8-dihydropyrimido[4,5-e][1,2,4]triazine,
3-methylthio-8-oxo-6-(2-cyclopropylmethoxyphenyl)-7,8-dihydropyrimido[4,5-e][1,2,4]triazine or
3-methylthio-8-oxo-6-(2-methoxyphenyl)-7,8-dihydropyrimido[4,5-e][1,2,4]triazine
or a pharmaceutically acceptable salt thereof.

16. A pharmaceutical composition for effecting bronchodilatation which comprises a compound according to claim 1 and a pharmaceutically acceptable carrier.

17. A pharmaceutical composition having anti-allergic activity which comprises a compound according to claim 1 and a pharmaceutically acceptable carrier.

18. A method of effecting bronchodilatation in a host in need thereof by administration of a non-toxic but effective amount of a compound according to claim 1.

19. A method of combatting allergic disease in a host in need thereof by administration of a non-toxic but effective amount of a compound according to claim 1.

* * * * *